(12) United States Patent
Zou et al.

(10) Patent No.: US 10,556,845 B2
(45) Date of Patent: Feb. 11, 2020

(54) SYSTEM AND PRODUCING METHOD FOR PREPARING ALKYLATED OIL BY USING SULFURIC ACID AS CATALYST

(71) Applicant: BEIJING UNIVERSITY OF CHEMICAL TECHNOLOGY, Beijing (CN)

(72) Inventors: Haikui Zou, Beijing (CN); Guangwen Chu, Beijing (CN); Jianfeng Chen, Beijing (CN); Yong Luo, Beijing (CN); Baochang Sun, Beijing (CN); Yang Xiang, Beijing (CN)

(73) Assignee: Beijing University of Chemical Technology, Beijing (CN)

( * ) Notice: Subject to any disclaimer, the term of this patent is extended or adjusted under 35 U.S.C. 154(b) by 0 days.

(21) Appl. No.: 15/575,425

(22) PCT Filed: May 20, 2016

(86) PCT No.: PCT/CN2016/082763
§ 371 (c)(1),
(2) Date: Nov. 20, 2017

(87) PCT Pub. No.: WO2016/184424
PCT Pub. Date: Nov. 24, 2016

(65) Prior Publication Data
US 2018/0354871 A1 Dec. 13, 2018

(30) Foreign Application Priority Data
May 21, 2015 (CN) .......................... 2015 1 0262784

(51) Int. Cl.
*C07C 2/62* (2006.01)
*B01D 3/14* (2006.01)
(Continued)

(52) U.S. Cl.
CPC .................. *C07C 2/62* (2013.01); *B01D 3/14* (2013.01); *B01D 3/143* (2013.01); *B01J 8/0055* (2013.01);
(Continued)

(58) Field of Classification Search
CPC ....... C07C 2/62; C07C 7/09; C07C 2527/054; C10G 29/205; B01J 8/0055;
(Continued)

(56) References Cited

U.S. PATENT DOCUMENTS 3,956,417 A * 5/1976 Franz ........................ C07C 2/62
585/706
2014/0128654 A1 * 5/2014 Fang ........................ B01J 19/28
585/730

FOREIGN PATENT DOCUMENTS

| CN | 101104570 | 1/2008 |
| CN | 105219428 | 1/2016 |
| WO | 2011015664 | 2/2011 |

OTHER PUBLICATIONS

Branzaru, "Introduction to Sulfuric Acid Alkylation Unit Process Design", Nov. 2001. (Year: 2001).*
(Continued)

*Primary Examiner* — Ali Z Fadhel
(74) *Attorney, Agent, or Firm* — Rankin, Hill & Clark LLP

(57) ABSTRACT

Disclosed are a system device for preparing an alkylate oil using a sulfuric acid catalyst and a manufacturing method thereof. The system device comprises a reactor unit (100), a catalyst and hydrocarbon circulation unit (200), a separator unit (300), an isobutane circulation unit (500) and a fractionator unit (400). The reactor unit (100) is connected and in communication with the catalyst and hydrocarbon circulation unit (200) and the separator unit (300) via channels respectively. The catalyst and hydrocarbon circulation unit
(Continued)

(200) is connected and in communication with the separator unit (300) via channels. The separator unit (300) is connected and in communication with the isobutane circulation unit (500) and the fractionator unit (400) via channels respectively. The catalyst and hydrocarbon circulation unit (200), the separator unit (300), the isobutane circulation unit (500) and the fractionator unit (400) are connected and in communication with the reactor unit (100) via channels respectively. The reactor unit (100) comprises at least a high gravity reactor. Due to the adopted high gravity reactor capable of highly reinforcing the mixing of materials under high viscosity, the system device can operate at a low temperature of −5° C. and prepare the alkylate oil having an octane number of 97-100 at an alkane/alkene ratio of 2-100.

10 Claims, 1 Drawing Sheet

(51) Int. Cl.
    B01J 8/00        (2006.01)
    C10G 29/20       (2006.01)
    B01J 19/00       (2006.01)
    C07C 7/09        (2006.01)

(52) U.S. Cl.
    CPC ....... *B01J 19/0013* (2013.01); *B01J 19/0053* (2013.01); *C07C 7/09* (2013.01); *C10G 29/205* (2013.01); *B01J 2219/00051* (2013.01); *B01J 2219/00162* (2013.01); *B01J 2219/00164* (2013.01); *C07C 2527/054* (2013.01); *Y02P 20/582* (2015.11)

(58) Field of Classification Search
    CPC ................ B01J 19/0053; B01J 19/0013; B01J 2219/00164; B01J 2219/00162; B01J 2219/00051; B01D 3/143; B01D 3/14; Y02P 20/582
    See application file for complete search history.

(56) References Cited

OTHER PUBLICATIONS

International Search Report filed in PCT/CN2016/082763 dated Aug. 26, 2016.

* cited by examiner

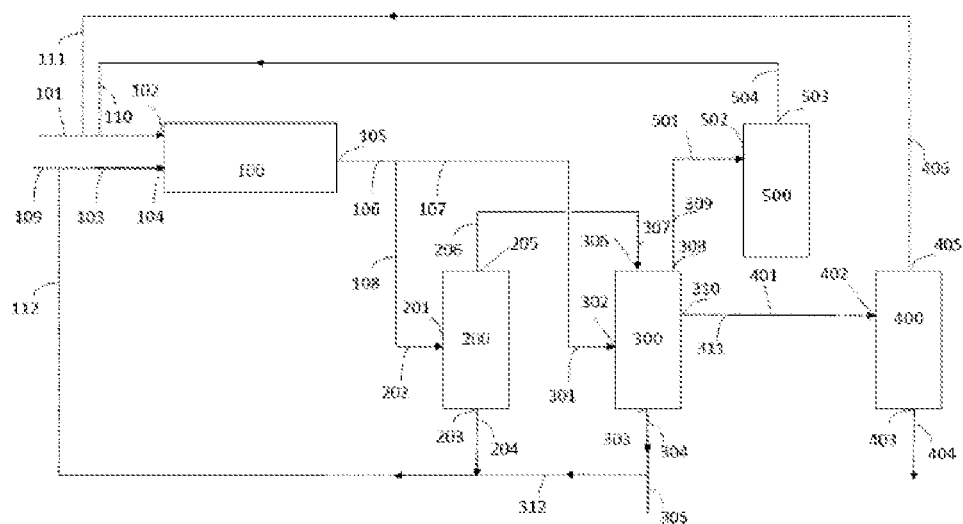

SYSTEM AND PRODUCING METHOD FOR PREPARING ALKYLATED OIL BY USING SULFURIC ACID AS CATALYST

FIELD OF THE INVENTION

The present invention relates to the technical field of preparation of alkylated oil, in particular to a system and a producing method for preparing alkylated oil by using sulfuric acid as a catalyst.

BACKGROUND OF THE INVENTION

With an increase of requirements on environmental protection, oil standards are increasingly higher. Newly formulated gasoline is required to satisfy the requirements such as high octane number, ultralow sulfur content, low alkene content and low aromatic hydrocarbon content. An alkylation process is a process of enabling light alkene to react with isobutane to produce an alkylated product containing rich isooctane. This alkylated product, almost all components of which are high-octane-number isoalkane, does not contain unideal components such as sulfur, alkene and aromatic hydrocarbon and is an ideal component of newly formulated gasoline.

Almost all alkylated oil is prepared by enabling isobutane and butene to react in condition of existence of an acidic catalyst. Sulfuric acid is one of major catalysts for alkylation reaction. However, the solubility of alkene and isoalkane which are the alkylation reaction raw materials in the catalyst, i.e. concentrated sulfuric acid is poor. Particularly, isobutane is very difficult to be dissolved in concentrated sulfuric acid. However, alkylation reaction is a quick reaction process. Therefore, full mixing of acid and hydrocarbon phases has a significant influence on product quality. Besides, although the solubility of alkene in concentrated sulfuric acid is slightly better than that of isobutane, alkene is very easily polymerized at temperature above 10° C. to produce polymers above C12. Besides, alkylation reaction is an exothermic reaction. If the reaction temperature is not properly controlled, the side reaction of alkene polymerization will be intensified. Therefore, temperature is also one of decisive variables in alkylation reaction. The lower the temperature is, the smaller the trend of the side reaction of alkene self-polymerization or reaction with acid to produce alkyl sulfate is. When the reaction is performed at lower temperature, a better conversion rate can be achieved and a high-quality alkylated product can be obtained. Therefore, the sulfuric acid alkylation process not only needs to realize full mixing of acid and hydrocarbon phases, but also needs to guarantee that alkylation reaction is performed at low temperature.

At present, a reactor adopted in the sulfuric acid alkylation process is a STRATCO reactor, in which a great number of tubular heat exchangers are disposed and materials are, by a mixing impeller, forced to circulate in mass so as to achieve reinforced mixing and heat transfer. Besides, it is beneficial to the quality of the alkylated product to increase a ratio of isobutane to alkene in the reactor, and a ratio of alkane to alkene and a ratio of acid to hydrocarbon in a reaction area can be improved through mass circulation of materials. However, since the viscosity of materials increases with the decrease of temperature, the difficulty in circulating the materials through the mixing impeller increases rapidly with the drop of the temperature of a reaction system, such that the system can be operated only at temperature above 0° C., and specifically at temperature above 4° C.

Therefore, there is a demand in industry for new high-efficiency processing methods and systems used for alkylating isoalkane.

SUMMARY OF THE INVENTION

One purpose of the present invention is to provide a system for preparing alkylated oil by using sulfuric acid as a catalyst.

Another purpose of the present invention is to provide a producing method for preparing alkylated oil by using sulfuric acid as a catalyst.

As compared with a STRATCO reaction system which is commonly used in industry, the production system provided by the present invention, because the circulation of catalyst and hydrocarbon adopts a forced circulating mode using a pump and a supergravity (referred to herein as "high-gravity") reactor, which can highly intensify mixing of materials under a situation of high viscosity is adopted, can be operated at lower temperature, specifically at low temperature of −5° C., and can prepare high-quality alkylated oil with an octane number of 97-100 within a ratio of alkane to alkene of 2-100.

In order to achieve the first purpose, the present invention adopts the following technical solution:

Provided is a system for preparing alkylated oil by using sulfuric acid as a catalyst, comprising a reactor unit, a catalyst and hydrocarbon circulating unit, a separator unit, an isobutane circulating unit and a fractionator unit. The reactor unit is respectively communicated with the catalyst and hydrocarbon circulating unit and the separator unit through pipes; the catalyst and hydrocarbon circulating unit is communicated with the separator unit through a pipe; the separator unit is respectively communicated with the isobutane circulating unit and the fractionator unit through pipes; the catalyst and hydrocarbon circulating unit, the separator unit, the isobutane circulating unit and the fractionator unit are respectively communicated with the reactor unit through pipes; and the reactor unit comprises at least one high-gravity reactor.

Preferably, the catalyst and hydrocarbon circulating unit comprises at least one circulating pump and at least one gas separation tank; the separator unit comprises at least one settling tank and at least one gas-liquid separation tank; the isobutane circulating unit comprises at least one gas compressor and at least one cooler; and the fractionator unit comprises at least one fractionating tower.

The reactor unit is used for enabling a material containing a catalyst sulfuric acid, a material containing isobutane and alkene and a circulating material containing the catalyst sulfuric acid and hydrocarbon to be in contact and react.

The catalyst and hydrocarbon circulating unit is used for pressurizing an effluent from the reactor by using a pump and then recirculating the effluent to enter the reactor unit, so as to guarantee that a ratio of acid to hydrocarbon and a ratio of alkane to alkene needed for reaction are within suitable ranges. In order to guarantee the normal operation of the circulating pump, at least one gas separation tank needs to be installed before the pump.

Preferably, the separator unit comprises a settler unit, a cyclone unit or a combination thereof; and preferably, the separator unit comprises one or more cyclone units provided at an upstream of the settler unit, and a device is provided to convey an effluent from the cyclone unit to the settler unit.

The separator unit is used for separating the effluent from the reactor into a catalyst phase, a hydrocarbon phase containing alkylated oil and a gas phase containing isobutane.

The isobutane circulating unit compresses and cools the gas phase isobutane into liquid isobutane, and the compressed and cooled liquid isobutane returns to an isobutane raw material storage tank of the reactor unit.

Preferably, the fractionator unit comprises one or more distillation subunits; and preferably, each distillation subunit comprises a main fractionating tower, an acid stripping tower and/or a depropanizing tower. The fractionator unit is used for fractionating the hydrocarbon phase containing alkylated oil into at least one material flow containing alkylated oil.

Preferably, the separator unit is located at a downstream of the reactor unit in a fluid flow path; and the fractionator unit is located at a downstream of the separator unit in the fluid flow path.

Preferably, a device used for recirculating at least one portion of the effluent from the reactor to the reactor unit is provided.

Preferably, a device used for recirculating at least one portion of the hydrocarbon phase containing alkylated oil to the reactor unit is provided.

In order to achieve the second purpose, the present invention adopts the following technical solution:

Provided is a producing method for preparing alkylated oil by using sulfuric acid as a catalyst by adopting the above system, comprising the following steps:

1) supplying a feed flow of hydrocarbon mixture at least containing isoalkane and alkene and a catalyst sulfuric acid to a reactor unit to perform alkylation reaction; supplying an effluent from the reactor unit after alkylation reaction to a catalyst and hydrocarbon circulating unit and a separator unit, wherein the feed flow of the hydrocarbon mixture and the catalyst comes from an internal circulation of the system and an external feed of the system;

2) pressurizing a lower-layer effluent of the catalyst and hydrocarbon circulating unit by using a circulating pump, then recirculating the effluent into the reactor unit and supplying an upper-layer effluent of the catalyst to the separator unit;

3) the separator unit separating the effluent entering the separator unit into a catalyst phase, a hydrocarbon phase containing alkylated oil and a gas phase; recirculating one portion of the catalyst phase separated by the separator unit to the reactor unit and removing the other portion as waste acid from the system; supplying the hydrocarbon phase containing alkylated oil separated by the separator unit to a fractionator unit; and supplying the gas phase separated by the separator unit to an isobutane circulating unit;

4) the isobutane circulating unit compressing and cooling the entering gas phase into liquid and recirculating the liquid to the reactor unit; and 5) the fractionator unit fractionating the influent hydrocarbon phase containing alkylated oil to obtain at least one product containing alkylated oil and a flow of other hydrocarbons, which are guided out as a lower-layer effluent; and recirculating an upper-layer effluent fractionated by the fractionator unit to the reactor unit for continuous reaction.

Preferably, in step 1), in the external feed of the system, the isoalkane is isobutane, the alkene is one or more of 2-butene, isobutene and 1-butene, and a molar ratio of isoalkane to alkene is above 1.

Preferably, in step 1), in the external feed of the system, the molar ratio of isoalkane to alkene is (1-100):1.

Preferably, in step 1), in the external feed of the system, the molar ratio of isoalkane to alkene is (1.5-20):1.

Preferably, in step 1), the temperature of alkylation reaction is −10-100° C. and the pressure of reaction is 0.1-5 MPa.

Preferably, in step 1), the temperature of alkylation reaction is −5-30° C. and the pressure of reaction is 0.1-1 MPa.

Preferably, in step 1), the producing method further comprises the step of recirculating a portion of the effluent of the reactor unit to the reactor unit.

Preferably, in step 3), the producing method further comprises the step of recirculating a portion of the hydrocarbon phase containing alkylated oil separated by the separator unit to the reactor unit.

Preferably, in step 1), a volume ratio of the internal circulation to the external feed of the system in the feed flow of the hydrocarbon mixture and the catalyst is (10-200):1; and the revolving speed of a rotor in the high-gravity reactor is 100-2850 rpm.

Preferably, in step 1), the volume ratio of the internal circulation to the external feed of the system in the feed flow of the hydrocarbon mixture and the catalyst is (10-40):1, and the revolving speed of the rotor in the high-gravity reactor is 150-1500 rpm.

Preferably, the alkylation process may be a semi-continuous process or a continuous process.

In the alkylation process, fresh isoalkane and alkene are supplied to this process according to a certain molar ratio. In case of continuous reaction, usually one or more materials containing isoalkane are recirculated to enable excessive isoalkane to return to the high-gravity reactor, so as to improve the ratio of alkane to alkene in the reactor.

Under a normal situation, a cooling pipe is provided in the fluid flow path of the rector to remove heat produced during alkylation reaction. As an alternative choice, an acid recirculating flow is cooled. The effluent of the reactor unit is mixture of catalyst and hydrocarbon phases, and the hydrocarbon phase contains alkylated oil and unreacted reactant (mainly isoalkane).

The separator unit plays a role of separating the effluent of the reactor into a catalyst phase, a hydrocarbon phase containing alkylated oil and a gas phase. A preferred separator unit is a settler unit, which is any one of separator units capable of separating two liquid phases under the effect of gravity. In fact, since the density of sulfuric acid is higher than the density of the hydrocarbon phase, the effluent of the reactor is usually separated into a hydrocarbon phase at an upper layer and a catalyst phase at a lower layer in the settler. The separator unit may also be a cyclone unit, a device for supplying at least one portion of the effluent of the reactor to the cyclone unit, and the cyclone unit separates the effluent of the reactor into a low-density effluent mainly containing a hydrocarbon phase containing alkylated oil and a high-density effluent mainly containing a catalyst phase. The cyclone unit may comprise one or more serially connected cyclone units.

The cyclone unit may be separately used, and the cyclone unit may also be additionally provided to the settler unit. Preferably, one or more cyclone units are provided at an upstream of the settler unit, and a device is provided to convey the low-density effluent mainly containing the hydrocarbon phase containing alkylated oil from the cyclone unit to the settler unit.

The high-density effluent mainly containing the catalyst phase from the cyclone unit may be recirculated to the reactor unit, and alternatively, it is combined with the catalyst phase obtained from the settler unit and then is recirculated.

In the present invention, a catalyst phase recirculating device is provided to recirculate the catalyst sulfuric acid from the settler unit to the reactor unit. Usually, in order to keep the activity of the catalyst, a portion of the catalyst sulfuric acid is removed as waste acid from the process, and fresh sulfuric acid is added to keep the level and activity of the catalyst unchanged.

A portion of the hydrocarbon phase containing alkylated oil obtained from the settler is supplied to the fractionator unit to obtain the product alkylated oil. The fractionator unit usually comprises one or more distillation subunits, each of which comprises a main fractionating tower, an acid stripping tower and/or a depropanizing tower.

After fractionation is performed, the obtained alkylated oil may be used for preparing aviation gasoline or be used as a gasoline blending component. The hydrocarbon phase may further contain a great amount of unreacted isoalkane. Preferably, at least one portion of the isoalkane is recirculated to the reactor unit through the device provided for recirculating the isoalkane from the fractionator unit to the reactor. By fractionating the hydrocarbon phase, a flow of other hydrocarbons such as a flow containing n-alkane may also be obtained.

A device is provided to enable the reactant and the catalyst to enter the reactor, to supply the effluent of the reactor to the separator unit, and to subsequently supply the hydrocarbon phase containing alkylated oil to the fractionator unit. Intermediate treatment may be performed to the effluent of the reactor, e.g., cooling or heating may be performed in a heat exchanger. This is also applicable to the hydrocarbon phase containing alkylated oil supplied to the fractionator unit. Usually, a device enabling the reactant and the catalyst to be guided into the reactor unit is provided to produce a circulation flow path of the reactant, the product and the catalyst. Besides, a device is provided to supply the effluent of the reactor from a reactor effluent outlet of the reactor unit to a reactor effluent inlet of the separator unit, wherein the separator unit is located at a downstream of the reactor unit in the fluid flow path. Besides, a device is provided to supply the hydrocarbon phase containing alkylated oil from an outlet of the hydrocarbon phase containing alkylated oil of the separator unit to an inlet of the hydrocarbon phase containing alkylated oil of the fractionator unit, wherein the fractionator unit is located at a downstream of the fractionator unit in the fluid flow path; and a catalyst recirculating device is provided to recirculate the catalyst from the settler unit to the reactor unit.

In the present invention, by providing the device for recirculating one portion of the effluent of the reactor from the reactor effluent outlet of the reactor unit to the reactor effluent inlet of the reactor unit, the device can recirculate one portion of the effluent of the reactor before the effluent of the reactor is separated into the catalyst phase and the hydrocarbon phase containing alkylated oil. As well, by providing a device for recirculating one portion of the hydrocarbon phase containing alkylated oil from the outlet of the hydrocarbon phase containing alkylated oil of the separator unit to a reactant outlet of the reactor unit, the device can recirculate one portion of the hydrocarbon phase containing alkylated oil before fractionation is performed.

The alkylation reactor unit of the present invention adopts the high-gravity reactor capable of highly intensifying the mixing efficiency of materials as the alkylation reactor, and a great amount of reactant is recirculated to improve the molar ratio of isoalkane to alkene, i.e., the molar ratio of the isoalkane to alkene can be improved to be above 20 by adopting a reactant recirculating mode. As compared with the mode of recirculating one portion of the effluent of the reactor, under a situation that the volume of the recirculating hydrocarbon is kept unchanged, by providing the device for recirculating the hydrocarbon phase containing alkylated oil, the volume of the material which needs to be recirculated is smaller.

Beneficial Effects of the Invention

The present invention has the following advantages:
1) By adopting the high-gravity reactor, the alkylation reactor unit of the present invention can enable the hydrocarbon phase and the catalyst phase to reach molecule-scale uniform mixing within very short time when the hydrocarbon phase and the catalyst phase enter the high-gravity reactor, can realize quick mass transfer of isoalkane from the hydrocarbon phase to the catalyst phase and quick dissipation of reaction heat, and thereby can prevent a local high-temperature area from being produced.
2) Since the circulation of the catalyst and hydrocarbon phases is realized by adopting the forced circulating mode using the pump in the present invention and the high-gravity reactor capable of highly intensifying the mixing of the materials under a situation of high viscosity is adopted, the producing method provided by the present invention can be operated at lower temperature, and specifically can be operated at low temperature of −5° C.
3) The high isoalkane-alkene ratio and the extremely high mixing efficiency in the present invention greatly improve the selectivity of alkylated oil, the amount of the formed oligomers or polymers is decreased at the same, and thus the present invention can prepare alkylated oil with an octane number of 97-100 within an alkane-alkene ratio range of 2-100.

DESCRIPTION OF THE DRAWINGS

The specific implementation modes of the present invention will be further described below in detail with reference to the drawings.

FIG. 1 illustrates a schematic diagram of a system for preparing alkylated oil by using sulfuric acid as a catalyst.

DESCRIPTION OF THE EMBODIMENTS

In order to more clearly describe the present invention, the present invention will be further described below with reference to the drawings in combination with the preferred embodiments. One skilled in the art shall understand that the content specifically described below is exemplary instead of restrictive and shall not limit the protection scope of the present invention.

Embodiment 1

A system for preparing alkylated oil by using sulfuric acid as a catalyst provided by the present invention is as illustrated in FIG. 1. The system comprises a reactor unit 100, a catalyst and hydrocarbon circulating unit 200, a separator unit 300, an isobutane circulating unit 500 and a fractionator unit 400; the reactor unit 100 is respectively communicated with the catalyst and hydrocarbon circulating unit 200 and the separator unit 300 through pipes; the catalyst and hydrocarbon circulating unit 200 is communicated with the separator unit 300 through a pipe; the separator unit 300 is respectively communicated with the isobutane circulating unit 500 and the fractionator unit 400 through pipes; the catalyst and hydrocarbon circulating unit 200, the separator unit 300, the isobutane circulating unit 500 and the fractionator unit 400 are respectively communicated with the reactor unit 100 through pipes; the reactor unit 100 comprises at least one high-gravity reactor; the catalyst and hydrocarbon circulating unit 200 comprises at least one circulating pump and at least one gas separation tank; the separator unit 300 comprises at least one settling tank and at least one gas-liquid separation tank; the isobutane circulating unit 500 comprises at least one gas compressor and at least cooler; and the fractionator unit 400 comprises at least one fractionating tower.

A specific process flow for preparing alkylated oil by using sulfuric acid as a catalyst by using the system provided by the present invention is as follow: hydrocarbon mixture containing alkene and isoalkane is supplied to the reactor unit 100 through a pipe 101 and a reactant inlet 102. The catalyst sulfuric acid enters the reactor unit through a pipe 103 and a catalyst inlet 104. In the reactor unit, the hydrocarbon mixture and the catalyst sulfuric acid are in contact and react with each other. Through a reactor effluent outlet 105, a reactor effluent containing the catalyst and the hydrocarbon is taken out from the reactor unit 100 and passes through a pipe 106, and then one portion enters the catalyst and hydrocarbon circulating unit 200 through a pipe 108, a pipe 202 and an inlet 201 of the catalyst and hydrocarbon circulating unit 200, wherein a low-layer effluent containing catalyst and hydrocarbon phases in the catalyst and hydrocarbon circulating unit 200 passes through an outlet 203 and a pipe 204, then is pressurized by using a pump, is recirculated into the pipe 103 through a pipe 112 and enters the reactor unit 100 through the inlet 104; and an upper-lay effluent containing a hydrocarbon phase passes through an outlet 205 and a pipe 206, enters an inlet pipe 307 and an inlet 306 of the separator unit 300 and then enters the separator unit 300. Other reactor effluents containing the catalyst and the hydrocarbon leaving the reactor unit pass through a pipe 107, then enter a pipe 301 and enter the separator unit 300 through an inlet 302 of the separator unit. In the separator unit 300, the reactor effluent containing the catalyst and the hydrocarbon is separated into a catalyst phase, a hydrocarbon phase containing alkylated oil and a gas phase containing isobutane. A portion of the catalyst is pumped into a pipe 312 and the pipe 112 from a catalyst outlet 303 in the bottom of the separator unit and a pipe 304 and is mixed with the mixture of the catalyst and the hydrocarbon, the mixture then enters the pipe 103 and enters the reactor unit 100, and the remaining catalyst is extracted as waste acid through a pipe 305 for further treatment. The separated gas phase containing isobutane is supplied to the isobutane circulating unit 500 through a gas phase outlet 308 of the separator unit 300, a pipe 309, a pipe 501 and an inlet 502, a liquid phase containing isobutane obtained after compression and cooling is supplied to a pipe 110 through an outlet 503 of the isobutane circulating unit and a pipe 504, and is recirculated to become a portion of the hydrocarbon mixture in the pipe 101. The hydrocarbon phase is extracted from the separator unit through an alkylate-oil-containing hydrocarbon phase outlet 310 of the separator unit 300 and a pipe 311, and is supplied to the fractionator unit 400 through a pipe 401 and an inlet 402. The lower-layer effluent, i.e., a product containing alkylated oil, is guided out from the outlet 403 in the bottom of the fractionator unit 400 through a pipe 404, and this product can be used for a fuel blending purpose. The upper-layer effluent, i.e., the hydrocarbon containing isobutane is extracted from an outlet 405 of the fractionator unit 400 and a pipe 406, and is recirculated through a pipe 111 to become a portion of the hydrocarbon mixture in the pipe 101. Other lows containing hydrocarbons (not shown) can be also obtained from the fractionator unit.

The fresh replenished catalyst sulfuric acid is supplied to the reactor unit 100 through a pipe 109 to guarantee that an acid-hydrocarbon ratio of the reactor unit is within a suitable range.

Embodiment 2

Operations are performed according to the flow illustrated in FIG. 1. The isoalkane is isobutane and the alkene is 2-butene. In the external feed of the system, an isoalkane-alkene ratio in hydrocarbon raw materials is 2:1, the reaction temperature is controlled to be 4-7° C., the pressure is 0.4 MPa and a volume ratio of the circulation to the feed of the hydrocarbon mixture and catalyst is 200:1. The reactor is a high-gravity reactor, the revolving speed of a rotor is 2850 rpm, the separator is a gravity settler, the fractionator is a packed tower, and an octane number of alkylated oil obtained from the bottom of the packed tower is 97.2 (research octane number).

Embodiment 3

Operations are performed according to the flow illustrated in FIG. 1. The isoalkane is isobutane and the alkene is mixture of 2-butene and isobutene. In the external feed of the system, an isoalkane-alkene ratio in hydrocarbon raw materials is 4:1, the reaction temperature is controlled to be 0-4° C., the pressure is 0.3 MPa and a volume ratio of the circulation to the feed of the hydrocarbon mixture and catalyst is 15:1. The reactor is a high-gravity reactor, the revolving speed of a rotor is 1500 rpm, the separator is a gravity settler, the fractionator is a packed tower, and an octane number of alkylated oil obtained from the bottom of the packed tower is 98.1 (research octane number).

Embodiment 4

Operations are performed according to the flow illustrated in FIG. 1. The isoalkane is isobutane and the alkene is mixture of 1-butene, 2-butene and isobutene. In the external feed of the system, an isoalkane-alkene ratio in hydrocarbon raw materials is 10:1, the reaction temperature is controlled to be 0-4° C., the pressure is 0.3 MPa and a volume ratio of the circulation to the feed of the hydrocarbon mixture and catalyst is 15:1. The reactor is a high-gravity reactor, the revolving speed of a rotor is 1800 rpm, the separator is a gravity settler, the fractionator is a packed tower, and an octane number of alkylated oil obtained from the bottom of the packed tower is 99.1 (research octane number).

Embodiment 5

Operations are performed according to the flow illustrated in FIG. 1. The isoalkane is isobutane and the alkene is 2-butene. In the external feed of the system, an isoalkane-alkene ratio in hydrocarbon raw materials is 2:1, the reaction temperature is controlled to be −4° C., the pressure is 0.1 MPa and a volume ratio of the circulation to the feed of the hydrocarbon mixture and catalyst is 18:1. The reactor is a high-gravity reactor, the revolving speed of a rotor is 1500 rpm, the separator is a gravity settler, the fractionator is a packed tower, and an octane number of alkylated oil obtained from the bottom of the packed tower is 97.4 (research octane number).

Embodiment 6

Operations are performed according to the flow illustrated in FIG. 1. The isoalkane is isobutane and the alkene is 2-butene. In the external feed of the system, an isoalkane-alkene ratio in hydrocarbon raw materials is 100:1, the reaction temperature is controlled to be 10° C., the pressure is 0.4 MPa and a volume ratio of the circulation to the feed of the hydrocarbon mixture and catalyst is 10:1. The reactor is a high-gravity reactor, the revolving speed of a rotor is 1800 rpm, the separator is a gravity settler, the fractionator is a packed tower, and an octane number of alkylated oil obtained from the bottom of the packed tower is 99.7 (research octane number).

Embodiment 7

Operations are performed according to the flow illustrated in FIG. 1. The isoalkane is isobutane and the alkene is 2-butene. In the external feed of the system, an isoalkane-alkene ratio in hydrocarbon raw materials is 10:1, the reaction temperature is controlled to be 10° C., the pressure is 0.4 MPa and a volume ratio of the circulation to the feed of the hydrocarbon mixture and catalyst is 40:1. The reactor is a high-gravity reactor, the revolving speed of a rotor is 1500 rpm, the separator is a gravity settler, the fractionator is a packed tower, and an octane number of alkylated oil obtained from the bottom of the packed tower is 99.8 (research octane number).

Embodiment 8

Operations are performed according to the flow illustrated in FIG. 1. The isoalkane is isobutane and the alkene is isobutene. In the external feed of the system, an isoalkane-alkene ratio in hydrocarbon raw materials is 15:1, the reaction temperature is controlled to be 20° C., the pressure is 0.5 MPa and a volume ratio of the circulation to the feed of the hydrocarbon mixture and catalyst is 50:1. The reactor is a high-gravity reactor, the revolving speed of a rotor is 100 rpm, the separator is a gravity settler, the fractionator is a packed tower, and an octane number of alkylated oil obtained from the bottom of the packed tower is 95.2 (research octane number).

Embodiment 9

Operations are performed according to the flow illustrated in FIG. 1. The isoalkane is isobutane and the alkene is mixture of 2-butene and 1-butene. In the external feed of the system, an isoalkane-alkene ratio in hydrocarbon raw materials is 1.5:1, the reaction temperature is controlled to be 4° C., the pressure is 0.3 MPa and a volume ratio of the circulation to the feed of the hydrocarbon mixture and catalyst is 200:1. The reactor is a high-gravity reactor, the revolving speed of a rotor is 2000 rpm, the separator is a gravity settler, the fractionator is a packed tower, and an octane number of alkylated oil obtained from the bottom of the packed tower is 97.1 (research octane number).

Embodiment 10

Operations are performed according to the flow illustrated in FIG. 1. The isoalkane is isobutane and the alkene is 1-butene. In the external feed of the system, an isoalkane-alkene ratio in hydrocarbon raw materials is 5:1, the reaction temperature is controlled to be 30° C., the pressure is 0.6 MPa and a volume ratio of the circulation to the feed of the hydrocarbon mixture and catalyst is 20:1. The reactor is a high-gravity reactor, the revolving speed of a rotor is 1500 rpm, the separator is a gravity settler, the fractionator is a packed tower, and an octane number of alkylated oil obtained from the bottom of the packed tower is 93.2 (research octane number).

Comparative Example 1

It is the same as embodiment 9, a difference lies in that a stirring reactor is used as the reactor unit for reaction, and an octane number of the obtained alkylated oil is 93.5 (research octane number).

Comparative Example 2

It is the same as embodiment 10, a difference lies in that a stirring reactor is used as the reactor unit for reaction, the stirring revolving speed is 1000 rpm and an octane number of the obtained alkylated oil is 91.3 (research octane number).

Obviously, the above-mentioned embodiments of the present invention are just examples for clearly describing the present invention instead of limiting the implementation modes of the present invention. One skilled in the art may make other different variations or changes on the basis of the above-mentioned description, all implementation modes cannot be enumerated herein, and obvious variations or changes derived from the technical solution of the present invention are also included in the protection scope of the present invention.

The invention claimed is:

1. A system for preparing alkylated oil by using sulfuric acid as a catalyst, comprising a reactor unit, a catalyst and hydrocarbon circulating unit, a separator unit, an isobutene circulating unit and a fractionator unit; wherein:
    the reactor unit is respectively communicated with the catalyst and hydrocarbon circulating unit and the separator unit through pipes;
    the catalyst and hydrocarbon circulating unit comprises at least one circulating pump and at least one gas separation tank, and is communicated with the separator unit through a pipe;
    the separator unit comprises a settler unit, a cyclone unit or a combination thereof, and is respectively communicated with the isobutene circulating unit and the fractionator unit through pipes;
    the isobutane circulating unit comprises at least one gas compressor and at least one cooler;
    the fractionator unit comprises at least one fractionating tower;
    the catalyst and hydrocarbon circulating unit, the separator unit, the isobutene circulating unit and the fractionator unit are respectively communicated with the reactor unit through pipes; and
    the reactor unit comprises at least one high-gravity reactor.

2. The system for preparing alkylated oil by using sulfuric acid as, a catalyst according to claim 1, wherein
    the separator unit comprises at least one settling tank and at least one gas-liquid separation tank.

3. The system for preparing alkylated oil by using sulfuric acid as a catalyst according to claim 1, wherein:

the separator unit comprises the settler unit and the cyclone unit, and a device is provided to convey an effluent from the cyclone unit to the settler unit.

4. The system for preparing alkylated oil by using sulfuric acid as a catalyst according to claim 1, wherein the fractionator unit comprises one or more distillation subunits; and each distillation subunit comprises a main fractionating tower, an acid stripping tower and/or a depropanizing tower.

5. The system for preparing alkylated oil by using sulfuric acid as a catalyst according to claim 1, wherein the separator unit is located at a downstream of the reactor unit in a fluid flow path; and the fractionator unit is located at a downstream of the separator unit the fluid flow path.

6. A producing method for preparing alkylated oil by using sulfuric acid as a catalyst by adopting the system according to claim 1, wherein the producing method comprises the following steps:

1) supplying a feed flow of hydrocarbon mixture at least containing isoalkane and alkene and a catalyst sulfuric acid to the reactor unit to perform alkylation reaction: supplying an effluent of the reactor unit after alkylation reaction to the catalyst and hydrocarbon circulating unit and the separator unit, wherein the feed flow of the hydrocarbon mixture and the catalyst comes from an internal circulation of the system and an external feed of the system;

2) pressurizing a lower-layer effluent of the catalyst and hydrocarbon circulating unit by using the at least one circulating pump, then recirculating the effluent into the reactor unit and supplying an upper-layer effluent of the catalyst to the separator unit;

3) the separator unit separating the effluent entering the separator unit into a catalyst phase, a hydrocarbon phase containing alkylated oil and a gas phase; recirculating one portion of the catalyst phase separated by the separator unit to the reactor unit and removing the other portion as waste acid from the system; supplying the hydrocarbon phase containing alkylated oil separated by the separator unit to the fractionator unit; and supplying the gas phase separated by the separator unit to the isobutane circulating unit;

4) the isobutane circulating unit compressing and cooling the entering gas phase into liquid and recirculating the liquid to the reactor unit; and 5) the fractionator unit fractionating the influent hydrocarbon phase containing alkylated oil to obtain at least one product containing alkylated oil and a flow of other hydrocarbons, which are guided out as a lower-layer effluent; and recirculating an upper-layer effluent fractionated by the fractionator unit to the reactor unit for continuous reaction.

7. The producing method for preparing alkylated oil by using sulfuric acid as a catalyst according to claim 6, wherein, in step 1), in the external feed of the system, the isoalkane is isobutane and the alkene is one or more of 2-butene, isobutene and 1-butene; a molar ratio of isoalkane to alkene is above 1.

8. The producing method for preparing alkylated oil by using sulfuric acid as a catalyst according to claim 6, wherein, in step 1) the temperature of alkylation reaction is −10-100° C. and the pressure of reaction is 0.1-5 MPa.

9. The product method for preparing alkylated oil by using sulfuric acid as a catalyst according to claim 6, wherein, in step 1) the producing method further comprises the step of recirculating a portion of the effluent of the reactor unit to the reactor unit; and in step 3), the producing method further comprises the step of recirculating a portion of the hydrocarbon phase containing alkylated oil separated by the separator unit to the reactor unit.

10. The producing method, for preparing alkylated oil by using sulfuric acid as a catalyst according to claim 6, wherein, in step 1), a volume ratio of the internal circulation to the external feed of the system in the feed flow of the hydrocarbon mixture and the catalyst is 10-200:1 and the revolving speed of a rotor in the high-gravity reactor is 100-2850 rpm.

* * * * *